United States Patent [19]

Gibbs

[11] Patent Number: 4,732,193
[45] Date of Patent: Mar. 22, 1988

[54] FLUID DRIVEN DEVICE CONNECTED INTO A FLUID SUPPLY SYSTEM

[76] Inventor: Alan H. Gibbs, 20125 S. Dixie Hwy., Miami, Fla. 33189

[21] Appl. No.: 590,841

[22] Filed: May 9, 1984

Related U.S. Application Data

[63] Continuation of Ser. No. 294,763, Aug. 20, 1981, abandoned, which is a continuation-in-part of Ser. No. 121,101, Feb. 13, 1980, abandoned.

[51] Int. Cl.$^4$ .......................................... F16K 31/122
[52] U.S. Cl. ................................................. 137; 239/99
[58] Field of Search ..................... 137/624.14; 239/99, 239/101

[56] References Cited

U.S. PATENT DOCUMENTS

| | | | |
|---|---|---|---|
| 1,796,940 | 3/1931 | Pottenger | 239/101 |
| 2,229,829 | 1/1941 | Watson | 137/624.14 |
| 3,583,440 | 11/1968 | Andersson | 137/624.14 |

FOREIGN PATENT DOCUMENTS

965330  4/1975  Canada ........................... 137/624.14

*Primary Examiner*—Alan Cohan
*Attorney, Agent, or Firm*—Eugene F. Malin

[57] ABSTRACT

A pressure wave motor that may be a fluid driven device with a continuous reciprocating driven member, the sole moving part, for connection into an appropriate non compressable fluid supply system that sustains pressure waves and that allows the reciprocating driven member to generate a usable harmonic pressure wave for use in sustaining continuous reciprocation of the driven member along with fluid flow. The pressure wave motor is driven solely by the fluid supply input fluid which is a liquid and the forces the input fluid generated by continuous reciprocation of the driven member for producing work without additional moving parts. The fluid supply system may be a normal household water supply system. The fluid driven device can produce a pulsating fluid output that may be used for cleaning and massaging. The fluid driven device includes a driven member cavity, the inlet connected to the cavity, a main outlet connected to the member cavity, a second outlet connected to the member cavity, and a control system. The pressure wave motor may be self-starting and the second outlet includes a variable fluid volume chamber between the member cavity and the second outlet. A variable valve may be used at the outlets to vary the rate of reciprocation of the driven member.

4 Claims, 48 Drawing Figures

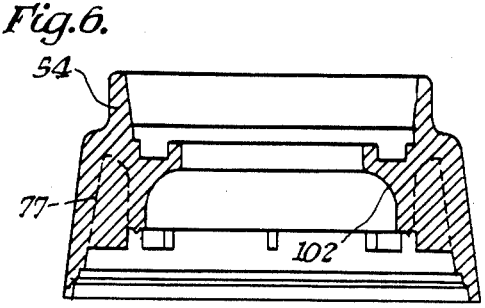
Fig.6.
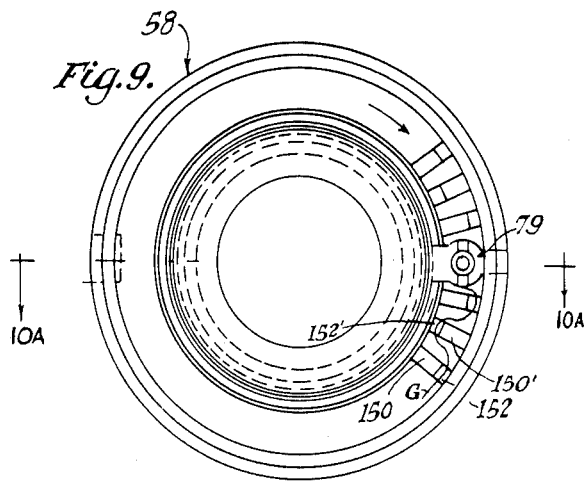
Fig.9.
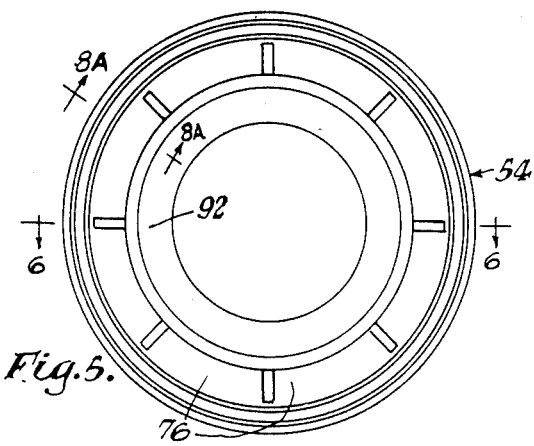
Fig.5.
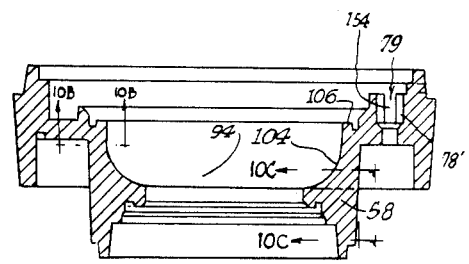
Fig.10A.
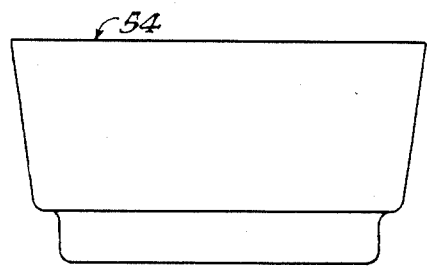
Fig.7.
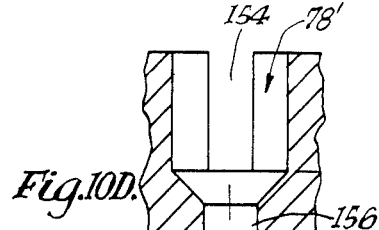
Fig.10D.
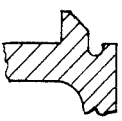
Fig.10B.
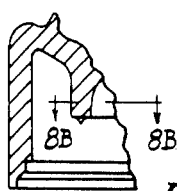
Fig.8A.      Fig.8B.
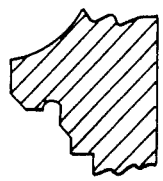
Fig.10C.

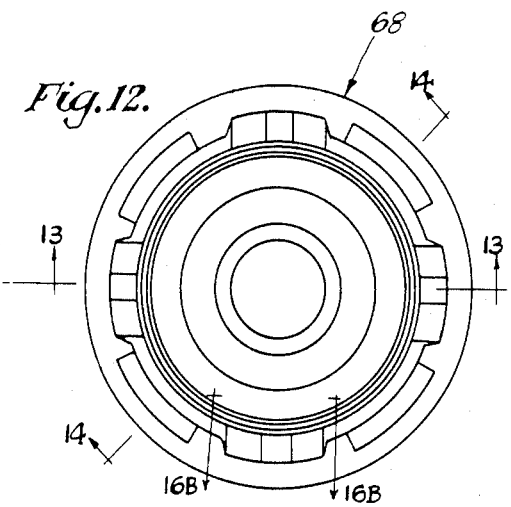
Fig.12.
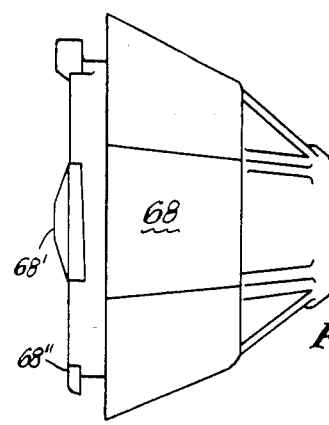
Fig.15.
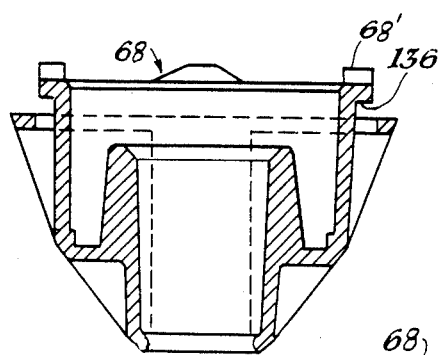
Fig.13.
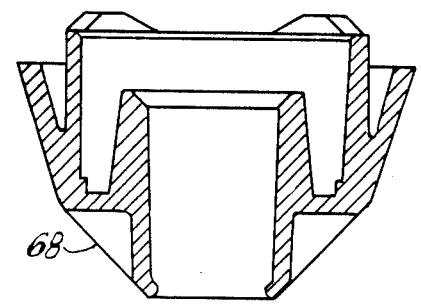
Fig.14.
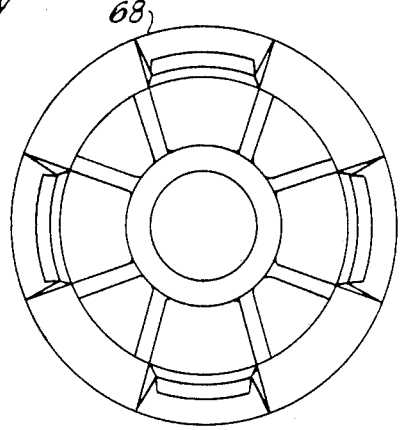
Fig.16A.
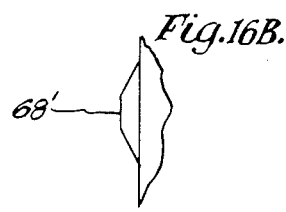
Fig.16B.
Fig.18.
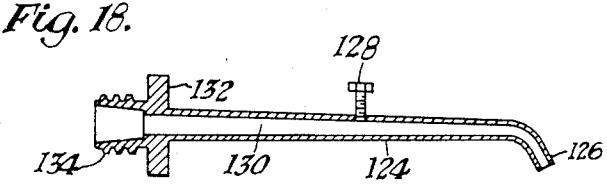
Fig.20.
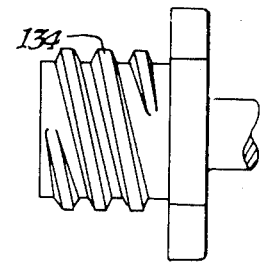

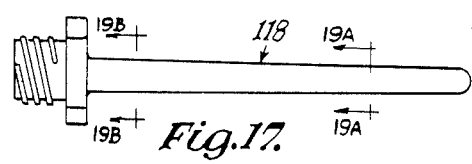
Fig.17. Fig.19A.

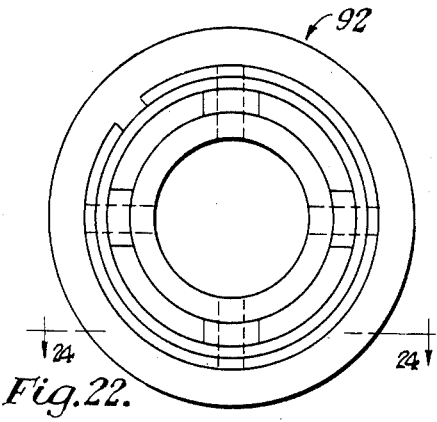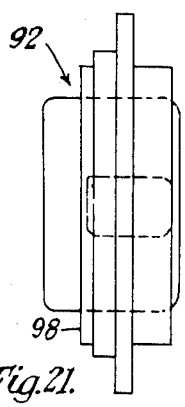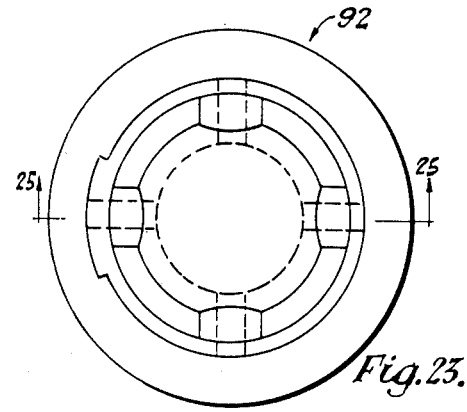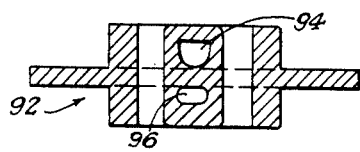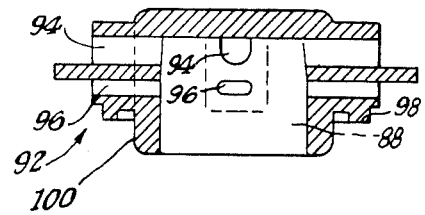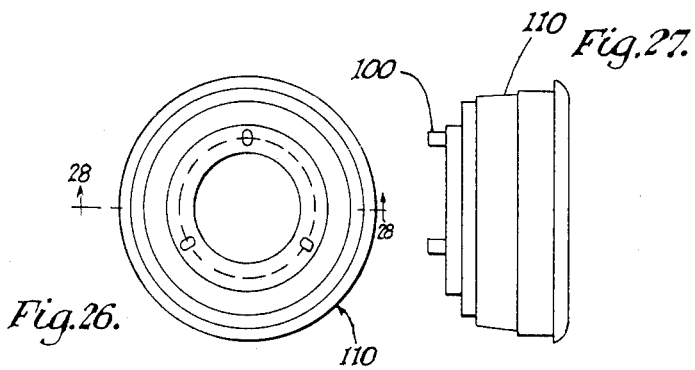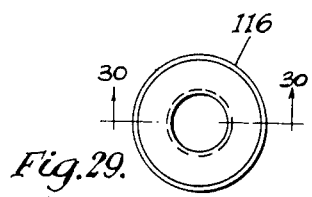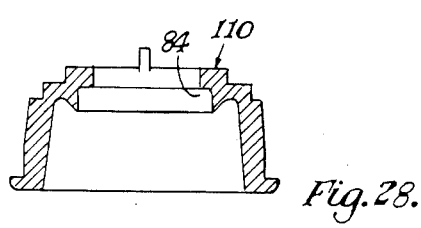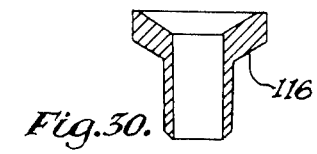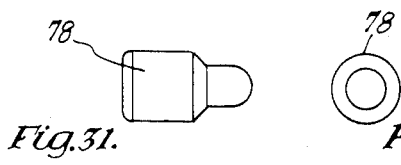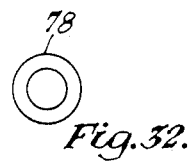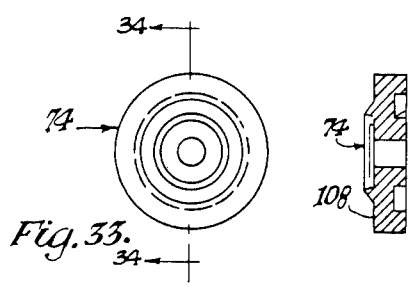

FLUID DRIVEN DEVICE CONNECTED INTO A FLUID SUPPLY SYSTEM

This is a continuation of Ser. No. 294,763, filed Aug. 20, 1981 and a continuation in part of application Ser. No. 121,101, filed 2/13/80 now abandoned which is incorporated herein by reference.

BACKGROUND OF THE INVENTION

This invention relates to a new and improved solely fluid driven motor or fluid driven device connected into a fluid supply system having a non compressable liquid and a pressure wave supportive structure. The motor or fluid driven device is self starting when the fluid supply input, non compressable liquid, is supplied. The motor, a fluid driven device, continuously reciprocates a driven member therein for providing useful work. A usable pulsating output fluid is discharged through the one outlet of the fluid driven device. The fluid driven device or motor and the fluid supply system include the reciprocating driven member or piston, a variable fluid volume chamber and control system. The fluid driven device can produce a pulsating fluid output that may be used for cleaning, especially for cleaning around and between teeth, as well as for cleaning and massaging gums.

In the past, devices employing pulsating jets of water for oral hygiene have employed a small reservoir for the water and have used an electrical pump to discharge a stream of water at a suitable velocity against the gums and teeth of the user. Various rotary driven members have been used to create a pulsating output. Other disclosures have been suggested employing fluid driven reciprocating valves to indirectly discharge a pulsating stream of fluid. The applicant's prior device disclosed in U.S. Pat. No. 3,499,440 and the prior art references of record cited therein, attempt to produce a pulsating fluid output stream. The 3,499,440 patent discloses a structure for discharging the pulsating fluid output through an intermediate piston chamber. The 3,499,440 patent relies on fluid flow variation to provide additional reciprocation and does not disclose the use of a variable fluid volume chamber including biasing system or an air biasing system to aid cyclic movement of a reciprocating driven member nor does it disclose the use of pressure waves to at least aid in producing continuous reciprocation of the driven member. The applicant herein discloses a control system for creating and using pressure waves, whether in the pressure wave motor and/or fluid supply system, and the variable capacity fluid cavity including a compressible resilient material such as an air chamber for at least aiding reciprocation and/or at least aiding in self-starting of the fluid control device. A great deal of the fluid passing through the applicant's prior art device was wasted through direct discharge. The discharged fluid was not usable for oral hygiene purposes. Further, the present invention as disclosed provides an extremely wide range of continuous pulsation for the discharge output from less than one pulse per second to more than several hundred or more cycles per second by varying the variable outlet control valves and by varying the size of the component parts of the device to provide a particular result.

SUMMARY OF THE INVENTION

The present invention relates to a new and improved motor that may be a fluid driven device with a continuous reciprocating driven member, the sole moving part in the motor. The pressure wave fluid supply system is a pressure wave sustaining fluid supply system that allows the reciprocating driven member to generate a usable harmonic that is a resonant, pressure wave and to use the result of the pressure wave to sustain continuous reciprocation of the driven member. The driven member may be in resonance with the harmonic pressure wave. A pressure wave sustaining fluid supply system is a system including structural material that sustains and/or reflects liquid pressure waves. The fluid flow and/or fluid pressure and the pressure waves are the sole driving forces. The motor or fluid driven device produces work without additional moving parts. The fluid driven device is readily attached to a normal household liquid supply system or special fluid supply system that sustain such a pressure wave. The fluid driven device can produce a pulsating fluid output that may be used for cleaning, especially for cleaning around and between teeth, as well as for cleaning and massaging gums. A permanent magnet may be placed in the driven member to produce electricity in an external coil in operable relationship to the magnetic field of the magnet.

The fluid driven device includes a driven member cavity, an inlet connected to the driven member cavity, and a first fluid flow path between the central portion of the driven member cavity and the first outlet. This fluid passes through the driven member cavity. A second fluid flow path is located between the driven member cavity or chamber and the second outlet. The second fluid flow path passes through the driven member cavity or chamber and into the variable fluid volume chamber located between the driven member cavity or chamber and the second outlet. A valve may be used at one or both of the two outlets to vary the rate per unit time, frequency per second of the movable driven member.

Since continuous reciprocation of the driven member is provided by the fluid driven device connected to supportive liquid supply system, the reciprocating driven member may provide useful work by discharging input fluid out of one of the two outlets in the form of a controlled pulsating fluid output. The fluid driven device is turned on and off by connecting it to a fluid supply system having a discharge control valve for controlling the liquid flow and shut off of liquid to the fluid driven device.

The method of operation of the fluid driven device appears to be initiated by opening a valve in the fluid supply system to provide liquid flow to engage the driven member in the housing of the fluid driven device. This initially causes the driven member to react and begin one or more reciprocating cycles. The reciprocation of the driven member creates pressure waves in the main cavity in the housing. The pressure waves move out through the inlet into the fluid supply system. The fluid supply system is of the type that sustains the movement of the pressure wave. One theory is that the reflected pressure waves build into a harmonic that is a resonant, wave that engages the moving reciprocating driven member to at least aid in further continuous reciprocation of the driven member. The particular state of the first two, three or more cycles of the operation of the liquid driven device and movement of the driven member are not known at this date because of the complexity in analyzing such movement. The driven member creates useful pressure waves that may be returned in harmonic that is a resonant wave form to provide additional power to at least aid in continuous reciprocation of the driven member. Therefore the return waves reinforce the imbalance condition for the driven member in the liquid flow to further drive the driven member or are reinforced to an extent to drive the driven member. It should be noted that the design of the device provides for a relatively imbalanced driven member condition so that when flowing fluid is introduced the driven member will reciprocate for a time in a manner that may gradually decrease the amplitude of the driven member after the initial inflow of liquid. The driven member will seek a steady state position. The pressure wave is additional force that may aid in operation.

The variable fluid volume chamber, an air chamber also aids in preventing the driven member from reaching a steady state position.

The variable fluid chamber traps compressable air therein to provide various functions including, but not limited to, providing a biasing function to aid in moving the driven member in the opposite direction after the driven member or piston portion of the driven member is moved into the variable flow chamber to compress the air therein. This variable fluid chamber also provides a flexible condition that seems to aid in the final and continuous reciprocation of the driven member. The variable fluid chamber may provide a time delay function.

The fluid driven device may be used as a pulsating oral hygiene device that is readily attached to a fluid supply or water supply downstream of a control valve, such as a household faucet. The pulsating oral hygiene device produces a pulsating, liquid discharge out of the outlet for cleaning teeth and massaging gums. The pulse rate and velocity may be varied.

In one embodiment, the inlet is positioned on top of the housing and the fluid flows down the outside portion of the inner housing to the inlet and the major portion of fluid passes directly out the first outlet located at the bottom of the device. A hose is connected to the outlet with a probe at the distal end. The probe may include a control valve to vary the pulse rate.

The driven member is located in the cavity in the central portion of the housing. This drive member includes a movable structure that is driven in a reciprocal movement back and forth in the cavity or chamber in the housing. The lower portion of the driven member includes a gating portion for creating the pulsating fluid output. The upper portion of the driven member is a piston movable in relation to the compressable air chamber.

The motor or fluid driven device may be a self-starting pressure wave motor. The motor or fluiddriven device may also be a liquid pressure resonant pressure wave driven device or motor. The motor is a continuously reciprocating liquid flow device which is connectable to the discharge of a pressure wave sustaining liquid supply system for supplying the sole input to solely reciprocate at least one driven member. The driven member is reciprocated by the input of liquid from the liquid supply system and the pressure waves generated by the driven member to provide work. The liquid flow device includes a driven member having a first end portion, a second end portion, and an intermediate portion and a means for housing said driven member. The means for housing has an inlet, a driven member cavity. There are two outlets, a first outlet and a second outlet. The liquid flow device also includes a control system including a shape and size means of said first end portion, a shape and size means of said second end portion, and an additional shape and size means. The driven member is operably positioned for reciprocation in operable relation to control liquid exiting said first outlet and said second outlet. The first end portion includes said shape and size means for controlling the liquid discharged from said first outlet. The second end portion includes said shape and size means for controlling the liquid discharge from said second outlet. The intermediate portion is positioned in operable relation to said inlet. The driven member includes said additional shape and size means for at least aiding continuous reciprocation of said driven member solely by the input of liquid flowing through said inlet onto said driven member and the forces generated by reciprocation of said driven member. The driven member together with said control system generates the forces from the liquid input from the liquid supply system to continuously reciprocate said driven member without additional control members. The liquid flow device is therefore a liquid pressure-resonant pressure wave driven device, that generates usable pressure waves. The liquid flow device is a self-starting device.

It is an object of this invention to provide a new and improved liquid pressure-resonant pressure wave driven motor.

It is another object of this invention to provide the sole continuously reciprocating driven member in a fluid driven device by utilizing pressure wave energy initiated by the flow of fluid from the supply system upon the reciprocating driven member.

It is another object of this invention to provide the sole continuously reciprocating driven member in a fluid driven device having a biasing means in working relation with the driven member.

It is another object of this invention to provide the sole continuously reciprocating driven member in a fluid driven device having a variable discharge at one of the two outlets to provide a control for providing self starting up and continuous reciprocation.

It is another object of this invention to provide a pulsating fluid discharge device driven solely by input fluid for discharging a portion of the input fluid out one outlet as a working, continuously pulsating fluid output.

It is an object of this invention to provide a continuously pulsating fluid discharge device driven solely by input fluid for cleaning around and between teeth as well as for cleaning and massaging gums.

It is another object of this invention to provide a liquid flow device having biasing cavity. It is another object of this invention to provide a liquid flow device having, two outputs, a driven member and a control means apparatus to discharge a continuously pulsating fluid for use out of one or both outlets.

It is another object of the present invention to provide an inexpensive solely fluid driven oral hygiene device which may be used to properly clean teeth and stimulate gums by utilizing only a liquid stream.

It is another object of the present invention to provide an improved solely liquid driven device for reciprocally moving the sole drive member having a gas compression chamber in the housing of the liquid driven device that allows a quantity of a liquid to move into the gas compression chamber to aid in operation of the cyclic movement of the driven member.

A further object of this invention is to provide a continuously pulsating solely liquid driven device with only one driven member for providing pulsating fluid output with one or more adjustable outlet control means to vary the rate of reciprocation of the driven member and the rate of the pulsating fluid output.

It is another object of this invention to provide a continuously pulsating solely liquid driven device with only one driven member having improved stability and efficiency.

It is another object of this invention to provide a continuously pulsating solely liquid driven device with only one driven member having a pulsation and non-pulsing mode of operation.

It is another object of this invention to provide a continuously pulsating solely liquid driven device with only one driven member that may be converted to operate without an output pulse for use as an aerating device.

An additional object of the present invention is to provide a continuously pulsating solely liquid driven device with only one driven member for oral hygiene use which is self-starting upon application of water from a valved faucet.

In accordance with these and other objects which will be apparent hereinafter, the instant invention will now be described with particular reference to the accompanying drawings.

BRIEF DESCRIPTION OF THE DRAWINGS

FIG. 5 is a scale bottom plan view of the upper housing of the present invention.

FIG. 6 is an upright scale elevational cross-section of FIG. 5 taken along lines 6—6.

FIG. 7 is a reversed scale elevational view of the upper housing of FIG. 6.

FIG. 8A is a scale view of the section of FIG. 5 taken along lines 8A—8A.

FIG. 8B is a scale view of the section of FIG. 8A taken along lines 8B—8B.

FIG. 9 is a scale top plan view of the lower housing of the present invention.

FIG. 10A is a scale cross-section of FIG. 9 taken along lines 10A—10A.

FIG. 10B is a scale cross-section of the section of FIG. 10A taken along lines 10B—10B.

FIG. 10C is a scale cross-section of the section of FIG. 10A taken along lines 10C—10C.

FIG. 10D is an enlarged cross-sectional view of the vent for discharge out a port through the lower housing of the present invention shown in FIGS. 9 and 10A.

FIG. 12 is a scale top plan view of a hose adapter for the present invention.

FIG. 13 is a scale elevational cross-section of FIG. 12 taken along lines 13—13.

FIG. 14 is a scale elevational cross-section of FIG. 12 taken along lines 14—14.

FIG. 15 is a scale elevational view of a hose adapter for the present invention shown in FIG. 12.

FIG. 16A is a scale bottom plan view of the hose adapter of FIG. 12.

FIG. 16B is a section of FIG. 12 taken along lines 16B—16B.

FIG. 17 is a scale elevational view of the probe used with the present invention.

FIG. 18 is a scale cross-sectional side view of the probe in FIG. 18 showing a control valve screw movable into and out of the fluid flow path.

FIG. 19A is a scale cross-sectional view of probe in FIG. 17 taken along lines 19A—19A.

FIG. 20 is a scale enlarged view of the threaded base of the probe in FIG. 17.

FIG. 21 is a scale elevation view of piston cylinder housing or upper piston cage of the present invention.

FIG. 22 is a scale bottom view of the piston cylinder housing of FIG. 21.

FIG. 23 is a scale top plan view of the piston cylinder housing of FIG. 21.

FIG. 24 is a scale cross sectional view of the piston cylinder housing taken along lines 24—24 of FIG. 22.

FIG. 25 is a scale cross-sectional view of the piston cylinder housing of FIG. 23 taken along the lines 25—25.

FIG. 26 is a scale top plan view of the lower piston cage of the present invention.

FIG. 27 is a scale elevational view of the lower piston cage in FIG. 26.

FIG. 28 is a scale cross-section view of FIG. 6 taken along lines 28—28.

FIG. 29 is a scale top plan view of the hose collet used with the present invention.

FIG. 30 is a scale cross-section of the hose collet of FIG. 29 taken along lines 30—30.

FIG. 31 is a scale elevational view of the pin of valve of metering member which is inserted in the vent shown in FIGS. 9 and 10A.

FIG. 32 is a scale bottom plan view of the pin of FIG. 31.

FIG. 33 is a scale top plan view of the piston of the movable member of the present invention.

FIG. 34 is a scale cross-sectional view of the piston in FIG. 33 taken along lines 34—34.

DESCRIPTION OF THE PREFERRED EMBODIMENT

Figure 1:
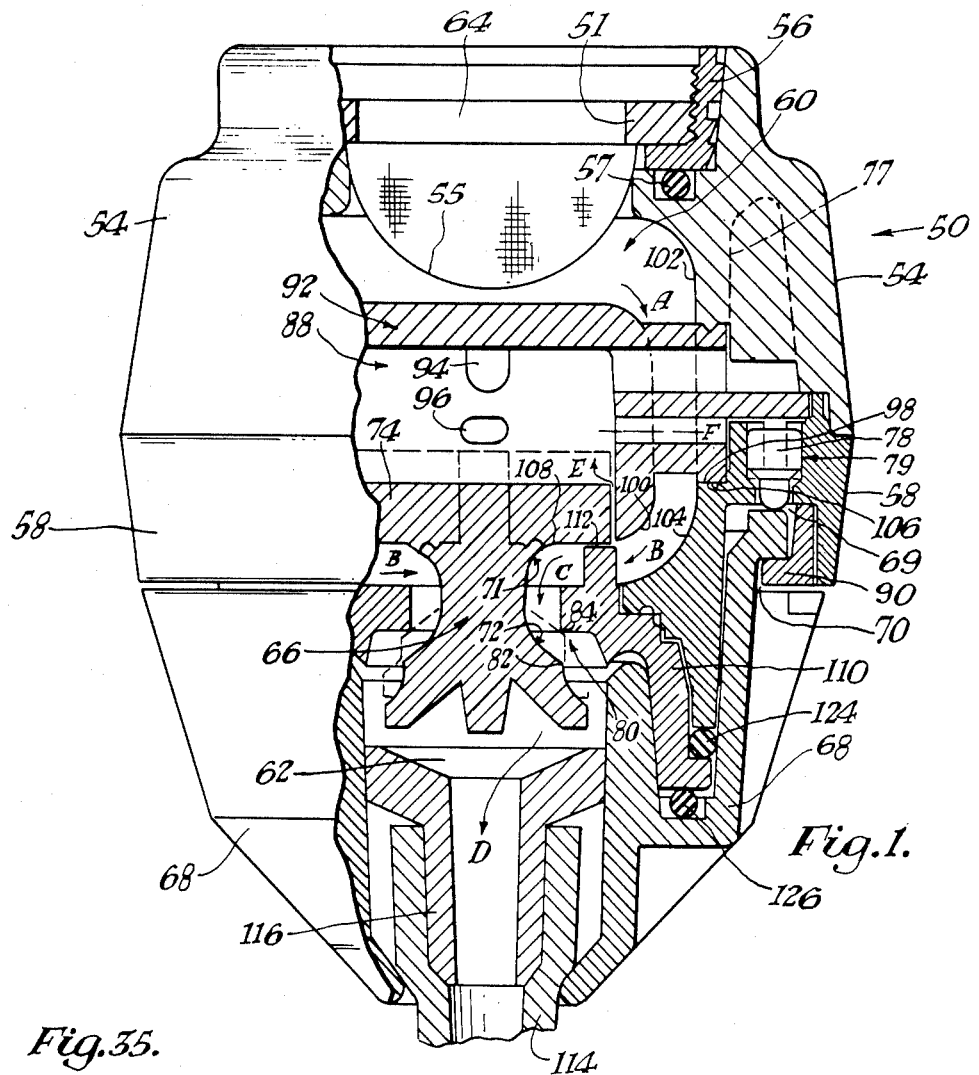
FIG. 1 is an elevational view of the present invention, a partially broken away sectional view illustrating the wave motor and the fluid driven device with the driven member in a flow-through position with a phantom outline of the driven member showing the gate closed. A proximal portion of an oral hygiene hose is illustrated.
Figures 35, 36:
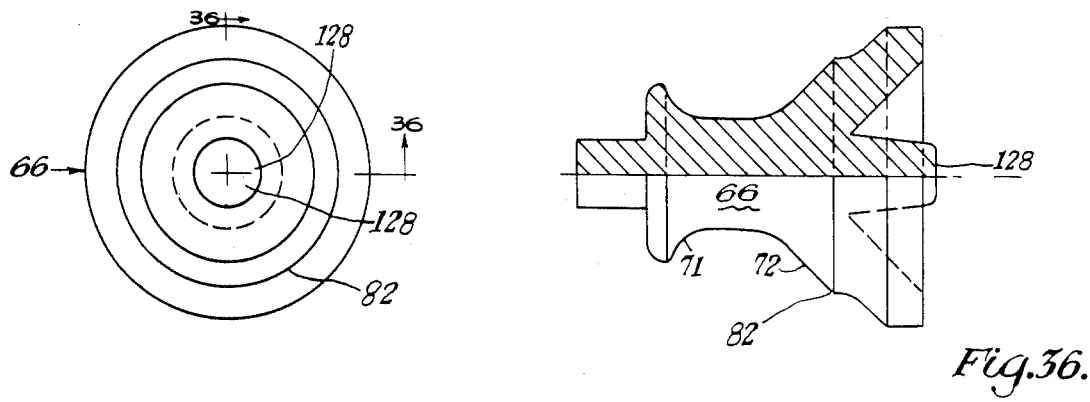
FIG. 35 is a scale top plan view of the driven member less the piston of the actuating apparatus of the present invention.
FIG. 36 is a scale side view partially in cross-section of the driven member less the piston shown in FIG. 35 taken along lines 36—36.
Figure 2:
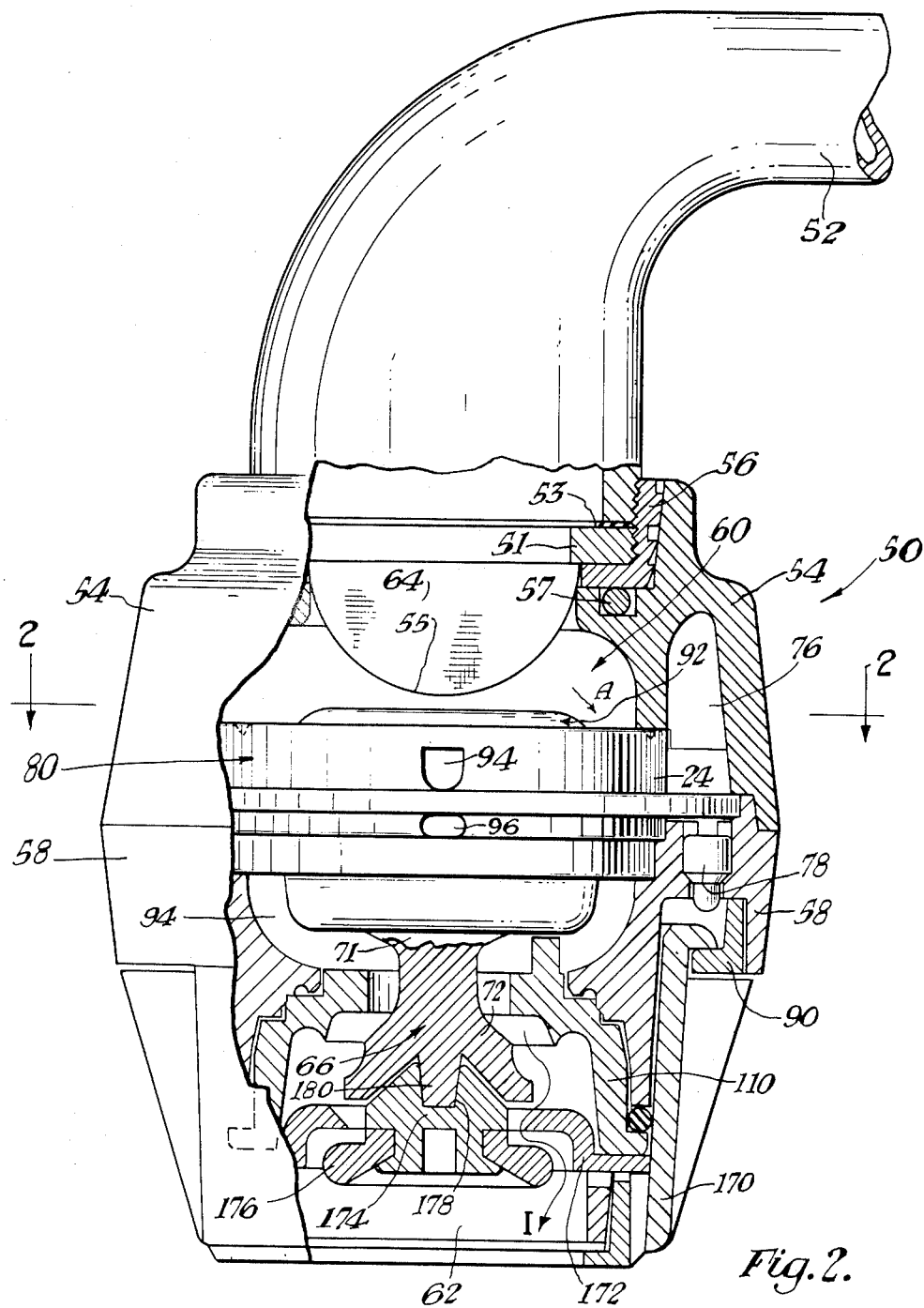
FIG. 2 is an elevational view of the present invention, partially broken away sectional view illustrating the fluid flow device connected to a faucet and with an aerating apparatus in place.
Figure 3:
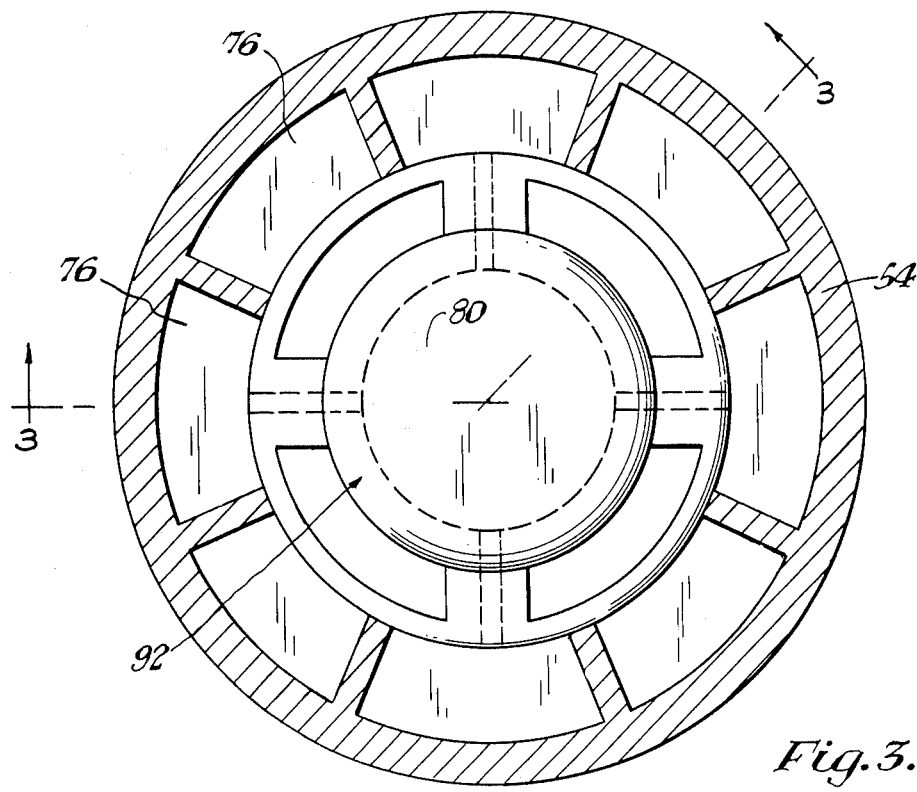
FIG. 3 is an illustration of a transverse cross-section taken along the line 2—2 of FIG. 2.
Figure 4:
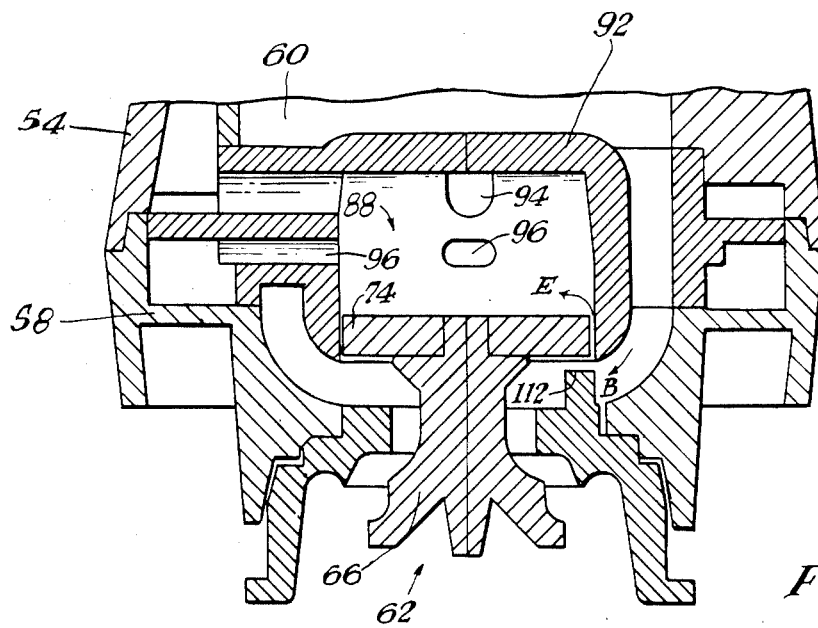
FIG. 4 is a partial view in cross-section view of FIG. 3 taken along the line 3—3 of FIG. 3.

Referring now in detail to the drawings, wherein an embodiment of the invention is shown, FIGS. 1, 3, and 4 illustrate an operable fluid driven device in a pulsating mode, and FIG. 2 illustrates the device in an aeration mode. FIGS. 5 through 39 are scale drawings of one working embodiment of the invention to fully disclose the device whose total precise theoretical operating characteristics may be undefined at this time.

Referring now in particular to FIG. 1, the oral hygiene device or the motor or fluid flow device generally designated as numeral 50 is attachable to a household faucet such as 52 in FIG. 2 having an output valve not shown. Typical pressure wave sustaining fluid supply systems are illustrated in household fluid supply systems in FIGS. 40, 41 and 42. The fluid flow device 50 in FIGS. 1 and 2 includes an upper body member 54, shown in detail in FIGS. 5 through 7 connected to an adapter 56 with a gasket 57. Adapter 56 may be used with the device to be secured to the faucet 52. Other shaped adapters may be used. A washer 51 may be used to prevent leaks. An additional flat washer 53 may also be used with the washer 51 to further secure the device to the faucet 52 as shown in FIG. 2. A filtering screen may be used to screen out foreign particles. A filtering screen is illustrated by number 55 in FIG. 1.

The fluid flow device includes the upper body member 54 and a lower body member 58 that is connected to the upper body member 54 by a well known connecting means. The lower body member is shown in detail in FIGS. 9 through 11. The various elements of the fluid flow device may be welded together and are releasably connected by mating portions. The upper and lower body members 54 and 58 define an elongated cavity 60 for holding or containing the drive system or means, the driven member 66 and the control system or means. The driven member is shown in detail in FIGS. 33 through 36.

The fluid flow device 50 is therefore connectable to the discharge of a variable flow fluid supply system. The fluid supply system supplies fluid to power the device 50 in order to reciprocate the driven member 66 and to provide pulsating fluid output from the device through the exit or output adjacent numeral 62. The device 50 includes a driven member and the variable volume fluid chamber located in cavity 60. The driven member is powered by the fluid input or water from the fluid supply system. The control system and the fluid flow and/or fluid pressure with resonant pressure waves reciprocates the driven member 66 which pulsates the fluid output of the greater portion of the fluid input as it moves out the first outlet 62. The body includes an inlet adjacent numeral 64, a first outlet at 62, central portion, and a main fluid path or conduit shown by arrows A, B, and C in FIG. 1. Arrow D shows the path of the greater portion of fluid flowing out toward the exit or first inlet 62. The central portion is fluidly connected to the inlet 64 by the upper portion of the main fluid conduit. The outlet 62 is fluidly connected to the central portion by the lower portion of the main fluid conduit in order to discharge the greater portion of the fluid input. The driven member is fluidly connected to the central portion of the device.

The driven member 66 and a control system which includes the shape and size of all portions of the driven member. The weight of the driven member may also be taken into account. The driven member in this case weighs approximately 1/10 of an ounce. The driven member 66 includes, among other things, the fluid or fluidic surfaces 71 and 72 that are part of the control system. Surface 71 is used to drive the driven body of the driven member upward. The surface or portion 72 is used to drive the driven body of the driven member downward. The fluid driven drive means includes, among other things, fluid flow means adjacent arrow B and biasing means. The fluid flow means is an orifice directing fluid against the driven member 66. The variable fluid volume chamber or biasing means shown herein as an air chamber 76 is shown in FIGS. 2 and 5 and in FIGS. 1 and 6 by dashed lines 77. The biasing means includes the air chamber or chambers 76 and cavity 88. The biasing means operates on piston 74 of driven member 66. The outlet control means illustrated by numeral 79 includes valve 78 shown in detail in FIGS. 31 and 32. The valve 78 is moved up by an upper portion 68'. The pulsating hose adapter 68 shown in FIGS. 12 through 16B may be used to open up the second fluid path as shown by arrow F in FIG. 1. The fluid flows in and around piston 74 as shown by arrow E. The outer circumference is spaced from the sides of the chamber 88. The smaller quantity of fluid exit out through the path designated by numbers 69 and 70. The exiting of the fluid along with the input liquid under pressure and the resonant pressure wave when generated and the biasing means allows the driven member to cycle in a repetitive cyclic movement over a range of fluid supply system shapes, materials and pressures.

The driven member 66 creates the pulsating output at exit 62. The driven member 66 includes a driven gating portion at 82 that is operatively connected adjacent the exit or outlet 62 to pulsate the fluid output before it moves out along a path shown by arrow D. The up and down movement of drive member 66 opens and closes the gate means 80 that includes the driven gate portion 82 and a base portion 84 on the lower piston cage member 110. The lower piston cage member 110 is shown in detail in FIGS. 26 through 28.

The driven member 66, the control system, the inlet, the two outlets and the biasing means are all operatively connected to power the cyclic movement of the driven member 66 and to pulsate the output fluid. Fluidic flow paths are provided to move the driven member 66 up and down in the body. The fluid flows from the orifice and flows out as indicated by arrow B from the circumscribed orifices. The fluid engages surface 71 of the driven member 66 to force it upward. The fluid from the orifice flows onto surface 72 when the driven member 66 is in an up position to move the driven member down. A greater portion of the fluid input passes by the driven member 66 and out through gate means 80 to the outlet 62. The biasing means may aid in continuing the cyclic movement. The outlet control means 79 varies the forces on at least a portion of the driven member, that is, the piston 74, to at least aid in continuing the cyclic movement by providing an unbalancing force on the driven member. The control fluid discharges out through outlet control means 79. The control means 79 includes valve 78 shown in FIGS. 31 and 32 and the valve cage 78' shown in FIG. 10D. A small quantity of fluid from the outlet control means then passes out of the device by moving from a point indicated by numeral 69 to a point indicated by numeral 70. The fluid will pass between the hose adapter 68 and the hose adapter positioning portion 90 or lug ring member 90 that is positioned between the lower body member 58 and the hose adapter. The lug ring member 90 shown in FIG. 38 may be welded to the lower body member 58.

Gaskets 124 may be placed between the lower piston cage 110 and the bottom concentric portion of the lower body portion 58 to prevent leaks. Gasket 126 may be placed between a portion of the hose adapter 68 and the lower piston cage 110 to prevent leaks. The various parts of the device may be constructed of ABS plastic or other suitable material.

In the pulsating mode, see FIGS. 1, 3 and 4, the piston cylinder housing 92 shown in detail in FIGS. 21 through 25 is disposed within the defined elongated cavity 60 as illustrated in FIGS. 1, 2, and 4. The piston cylinder housing 92 includes a piston chamber 88, air chamber connection or conduit 94 and outlet control connection or passage 96. The cylinder housing 92 has a support portion 98. Further, the piston cylinder housing 92 has an outer fluidic surface 100 that provides a fluid path between the outer fluid surface 100 and the inside wall 102 of the upper body member 54 and the inside wall surface 104 of the lower body member 58. The support portion 98 is supported upon a concentric lip 106 of the lower body member 58.

The piston cylinder housing 92 allows the piston 74 to move therein and provide a biasing means to aid in cyclic movement of the driven member 66. The driven member 66 is fixedly connected to the piston 74. The piston 74 is bottomed out when the lower surface 108 contacts the upper surface portion 112 of the lower piston cage 110 shown in FIGS. 26 through 28.

The hose adapter 68 not only lifts valve member 78 to an open position as shown in FIG. 1, but also connects the hose 114, preferably a urethane tubing having a length of about twenty-four inches, to the device. The tube 114 may include a proximal adapter member 116 also shown in FIGS. 29 and 30 that lies between the hose adapter 68 and the proximal end of the hose 114. The distal or other end of the hose 114 shown in FIG. 37 includes a probe 118. The probe may be connected to the distal end of the hose 114 by a probe mount body 120 with a probe mount cover 122.

The probe shown in FIGS. 17 through 20 includes and elongated tapered nozzle 124 with a turned end portion 126. A screw means 128 is moveable into and out of the probe channel 130 to regulate the rate of the pulsating fluid jetting out of the end 126. The screw 128 may be used to control the rate of pulse when the supply fluid from a faucet is at a generally steady pressure and quantity of flow. Screw 128 may be located in member 122 and 122' in order to control the rate of pulse. Screw 128 may also reduce the quantity of flow. The distal end of the probe includes a flange 132 and a screw meeting means 134. The screw means meets with the probe by the mount body 120 shown in FIG. 37. The sizing and scale of the device may be as shown in FIGS. 17 through 20.

Figure 38:
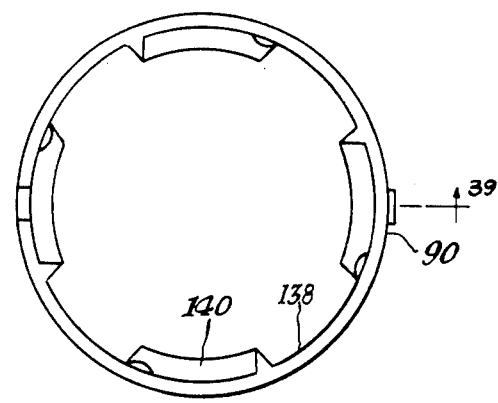
FIG. 38 is a scale top view of the hose adapter positioning portion or member.
Figure 37:
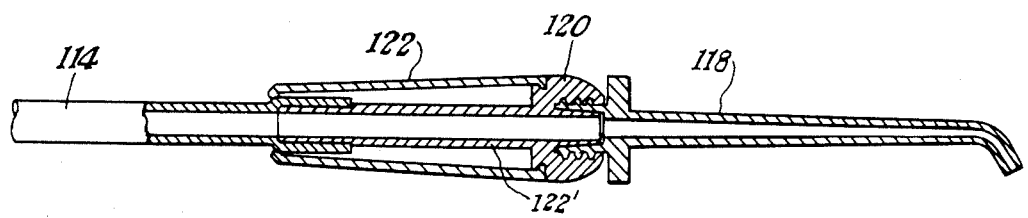
FIG. 37 is a scale side elevational view of the probe, probe handle and a portion of the hose in cross-section.
Figure 39:
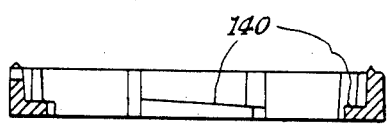
FIG. 39 is a cross-sectional side view taken along lines 39—39 and looks in the direction of the arrows in FIG. 38.
Figure 19B:
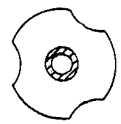
FIG. 19B is a scale cross-sectional view of the probe in FIG. 17 taken along lines 19B—19B.

When the hose is mounted by the hose adapter 68, the hose adapter shown in FIGS. 12 through 16B includes an upper lifting portion 68'. The lifting portion 68' is an actuating device that lifts the valve 78 in order to initiate the control means to release fluid to control the cyclic movement of the device. The actuating member 68' is moved into position with the hose adapter 68. The hose adapter (see FIG. 13) and the shelf portion 136 moves through openings 138 shown in FIG. 38 in order that the support shelf 136 fits on top of the ring support member 140. It should be noted that support shelf 140 holds the hose adapter in position as shown in FIGS. 38, 39, and 13. The tolerances may even be made tighter than shown in the drawings to frictionally secure the hose adapter to the ring member 90.

It should be noted that the fluid driven fluid flow control device has a pulsating mode when lower end of member 78 in FIG. 31 is in contact with the top of member 68' in FIG. 15 and a non-pulsating mode when the lower end of member 78 in FIG. 31 is in contact with the top of member 68" in FIG. 15.

Figure 11:
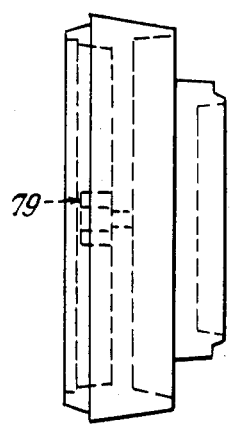
FIG. 11 is a scale right side elevation of FIG. 9.

Referring now to the lower housing member 58 shown in FIGS. 9, 10A, 10B, 10C, 10D, as well as FIG. 11, the control outlet fluid that moves out of the upper piston cage 88 through openings 96, as shown by arrow F in the vent in FIG. 1, will move through a tortuous path around wall portions 150 through cut down channels 152, as shown in FIG. 9. The fluid will move through the tortuous path as shown by arrow G in FIG. 9 and moves through slot 154 in FIG. 10A into the valve cage 78'. When the valve member 78 is lifted up, the fluid will move out through channel 156 shown by arrow H in FIG. 10D.

To convert the device to an aeration device, the hose adapter 68, gasket 126, hose 114, proximal adapter 116, and the probe 118 are removed from the device. As shown in FIG. 2, the aeration holder 170 is connected to lug ring 90. The holder 170 is connected to member 172 which in turn is connected to damper 174 with aeration fixture 176. The damper 174 includes a water cavity 178 in which projection 180 of member 66 will move to fix the position of 66 as shown in FIG. 2. The water will flow along path shown by arrow I to provide aerated water output by well known means.

The scale drawings are filed in this case because of the fluidic operation of the device whose mathematical formula and complete theory of operations is not known at this date.

Figure 40:
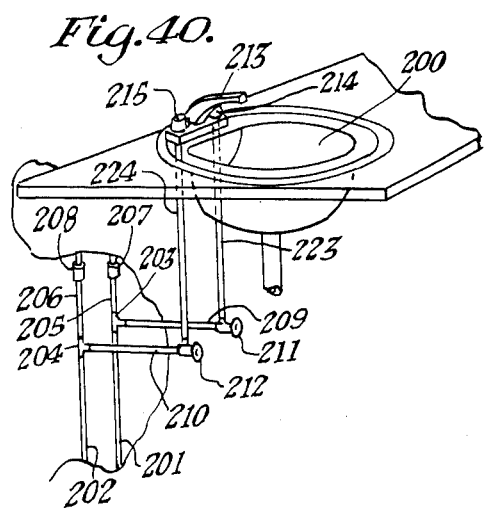
FIG. 40 is a normal household fluid supply.

FIG. 40 is a common bathroom fixture including a sink 200, cold water input line 201 of ½" diameter line of steel, plastic or copper pipe and hot water input line 202 of a ½" inside diameter line of steel or copper pipe or plastic (PVC). T-fittings 203 and 204 of similar material lead to air chambers 205 and 206 of ½" inside diameter or larger with caps 207 and 208. Lines 209 and 210 of similar materials are connected to valves 211 and 212 of similar material which are in turn connected to faucet 213 of similar material and valves 214 and 215 of similar material. The valves are in turn connected to pipes 223 and 224 of similar material of ⅜" outside diameter. A ¼ inch inside diameter fitting may be used to connect the faucet to the conduit. FIG. 40 shows a supportive fluid supply system that is connected to main city water lines.

Figure 41:
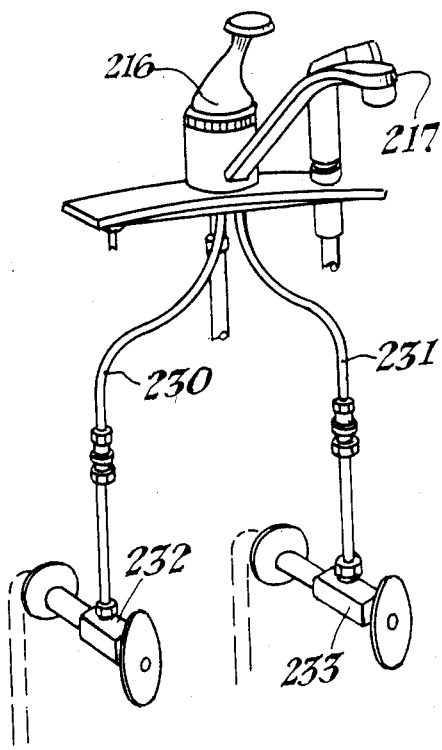
FIG. 41 is another fluid supply.
Figure 42:
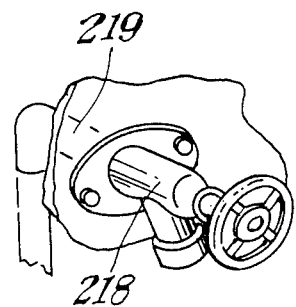
FIG. 42 is another fluid supply.

FIG. 41 shows pipes 230 and 231 of ⅜" outside diameter of the same material as 223 and 224 and valves 232 and 233 are similar to valves 211 and 212. FIG. 42 shows an outside valve 218 of similar material connected to a ¾ inch inside diameter pipe 219.

It should be noted the fluid driven device may be constructed of BORG-WARNER D.F.A.R. CYCO-LAC T2502 or ABS plastic.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A device for producing pressure pulses of liquid comprising:
   (a) a housing having a liquid inlet, a liquid outlet, and a chamber therebetween;
   (b) said chamber includes an inline valve device in said housing comprising a body means having a piston chamber portion and a valve seat portion, said inline valve device with an inlet connected to the liquid inlet, an outlet connected to the liquid outlet and said valve seat portion therebetween;
   a valve device having a valve head cooperating with the outlet side of said valve seat portion for controlling flow between said inlet and said outlet and a piston portion on the inlet side of said valve seat portion connected to said valve head reciprocating in said piston chamber portion;
   said piston portion having a larger area than said valve head so that inlet pressure on the side of said piston portion facing said valve seat portion acts in a direction to close said inline valve device;
   restricted passage means communicating inlet pressure from one side to the other side of said piston portion so as to aid in operation of said inline valve device;
   restriction means communicating said piston chamber portion on said other side of said piston portion with atmosphere; and
   a closed air chamber communicating with said piston chamber portion on said other side of the piston;
   said air chamber, said restricted passage means, said restriction means and said valve device so dimensioned as to cause oscillation of said valve device and thus a pulsating flow of liquid at said liquid outlet in response to connection to a source of pressurized liquid at said liquid inlet.

2. A device as set forth in claim 1 including:
   an adjustable valve in said restriction means to aid in securing oscillation of said valve device and pressure pulses of liquid.

3. A device as set forth in claim 1 including:
   a hose connected to said liquid outlet for cleaning between such places as the gums and teeth with a pulsating flow of liquid generated by a source of pressurized liquid, while providing a continuous alternative liquid flow path through said restrition means.

4. A method of aiding oscillation of the movable member in a fluid housing cavity in an oscillator, by a resonant pressure wave to control continuous movement of the movable member at a resonant pressure wave frequency, comprising the steps of:
   connecting said oscillator and said movable member to a pressurized fluid source to pass said fluid through said housing cavity,
   connecting said oscillator to a fluid resonant pressure wave resonator means for controlling the frequency of oscillation of said movable member,
   initiating oscillation of said member by passing said pressurized fluid through said housing cavity in contact with said movable member,
   selecting and providing a generally continuous resonant pressure wave for controlling the frequency of oscillation of said movable member,
   continuously transferring said resonant pressure wave from said resonator means into contact with said movable member for interaction to control continuous oscillation of said movable member at a resonant pressure wave frequency when under the influence of said pressurized fluid source,
   providing generally smooth continuous periodic movement of said movable member in said housing cavity,
   generating pressure waves from said movable member,
   transferring said pressure waves to said resonator means to generate said resonant pressure wave in said resonant means to provide a feedback control;
   providing an inlet and a first outlet and a second outlet in said housing cavity,
   providing a conduit to transfer said fluid and said resonant pressure wave into engagement with said movable member through said inlet,
   positioning at least a portion of said movable member between said inlet and both said first outlet and said second outlet, and positioning said movable member between said first outlet and said second outlet;
   transferring said pressure waves to said resonator means and transferring said resonant pressure wave to and from said movable member in an unrestricted manner.

* * * * *